United States Patent
Hsu

(10) Patent No.: US 10,181,189 B2
(45) Date of Patent: Jan. 15, 2019

(54) QUANTITATIVE METHOD FOR NUCLEAR MEDICINE HEART IMAGE AND ELECTRONIC DEVICE

(71) Applicants: Bailing Hsu, Taipei (TW); Bailing Cloud Biomedical Technologies Innovation (BCBTI), Taipei (TW)

(72) Inventor: Bailing Hsu, Taipei (TW)

(73) Assignees: Bailing Hsu, New Taipei (TW); BAILING CLOUD BIOMEDICAL TECHNOLOGIES INNOVATION(BCBTI), New Taipei (TW)

( * ) Notice: Subject to any disclaimer, the term of this patent is extended or adjusted under 35 U.S.C. 154(b) by 53 days.

(21) Appl. No.: 15/650,985

(22) Filed: Jul. 17, 2017

(65) Prior Publication Data
US 2018/0018768 A1    Jan. 18, 2018

(30) Foreign Application Priority Data

Jul. 18, 2016  (TW) .............................. 105122605 A

(51) Int. Cl.
| | |
|---|---|
| G06T 7/00 | (2017.01) |
| A61B 6/03 | (2006.01) |
| G01T 1/161 | (2006.01) |
| G01T 1/164 | (2006.01) |

(52) U.S. Cl.
CPC ............ *G06T 7/0012* (2013.01); *A61B 6/037* (2013.01); *G01T 1/161* (2013.01); *G01T 1/1642* (2013.01); *G06T 2207/30048* (2013.01)

(58) Field of Classification Search
CPC ........ A61B 6/037; G01T 1/161; G01T 1/1642
See application file for complete search history.

(56) References Cited

U.S. PATENT DOCUMENTS

| | | | |
|---|---|---|---|
| 2009/0050811 A1* | 2/2009 | Barrett .................. | G01T 1/1642 250/363.04 |
| 2014/0341453 A1* | 11/2014 | Hsu ...................... | A61B 6/5264 382/131 |
| 2017/0039706 A1* | 2/2017 | Mikhno ................. | A61B 6/037 |
| 2017/0042495 A1* | 2/2017 | Matsuzaki .............. | A61B 5/00 |

* cited by examiner

*Primary Examiner* — Edward Park
(74) *Attorney, Agent, or Firm* — JCIPRNET

(57) ABSTRACT

A quantitative method for nuclear medicine heart image and an electronic device are provided. The method is adapted for multi-pinhole SPECT images or SPECT/CT images. The method includes a radionuclide physical decay correction, a scatter correction, a geometry distortion correction, a data truncation compensation, a tissue attenuation correction, an image space resolution recovery, a noise removal, a pixel value conversion, a myocardial blood flow quantitative calculation, an intra-scan patient movement correction and a blood flow condition evaluation. Accordingly, a quantitative SPECT reconstructed image of a heart is obtained, and an absolute quantization of the myocardial blood flow is calculated to measure the myocardial blood flow quantitatively according to the quantitative SPECT reconstructed image. In addition, a blood flow condition diagram according to a number of indicators is established, and a myocardial blood flow condition is evaluated according to a quantization result of myocardial blood flow and the blood flow condition diagram.

13 Claims, 13 Drawing Sheets

| Carry out a radionuclide physical decay correction, wherein a radionuclide decay correction coefficient at each dynamic time point in a dynamic SPECT collection is calculated based on a time point of starting the dynamic SPECT collection, a duration of the collection, and a half-life of a marker imaging tracer, and a radioactive count in an original projection image is corrected based on the radionuclide decay correction coefficient | S1201 |

↓

| Carry out a scatter correction, wherein a scatter component in the original projection image is calculated based on a scatter energy window, and the scatter component is subtracted from the original projection image to obtain the original projection image after the scatter correction | S1203 |

↓

| Carry out a geometry distortion correction, wherein a plurality of normal rays are translated and a first coordinate conversion calculation is performed through a forward projection and a back projection based on a geometric position of a pinhole and a detector corresponding to the center of the SPECT reconstructed image, so as to obtain correct positions of an oblique ray at the detector and the SPECT reconstructed image and correct a geometry distortion in the SPECT reconstructed image resulting from the oblique ray | S1205 |

↓

| Carry out a data truncation compensation, wherein a truncated area in a field of view of the original projection image is calculated by expanding a field of view of the SPECT reconstructed image and performing another front projection, a count of a truncated area in an image projected from the SPECT reconstructed image is combined with the original projection image to expand a field of view of the original projection image, and iteration is performed with the original projection image having an expanded field of view as an input to expand the field of view of the SPECT reconstructed image until convergence is reached, so as to correct an artifact resulting from a data truncation in the SPECT reconstructed image | S1207 |

↓

| Carry out a tissue attenuation correction, wherein a tissue attenuation matrix is established by calculating an attenuation value of each ray from the pinhole to the detector based on a tissue attenuation diagram, and underestimation of a marker imaging tracer extraction activity of a heart and marker imaging tracer extraction activities of parts other than the heart caused by tissue attenuation are corrected based on the tissue attenuation matrix, so as to correct the tissue attenuation in the SPECT reconstructed image | S1209 |

↓

FIG. 12A

QUANTITATIVE METHOD FOR NUCLEAR MEDICINE HEART IMAGE AND ELECTRONIC DEVICE

CROSS-REFERENCE TO RELATED APPLICATION

This application claims the priority benefit of Taiwan application serial no. 105122605, filed on Jul. 18, 2016. The entirety of the above-mentioned patent application is hereby incorporated by reference herein and made a part of this specification.

BACKGROUND OF THE INVENTION

1. Field of the Invention

The invention relates to a quantitative method for a nuclear medicine heart image, and particularly relates to a method for a multi-pinhole SPECT or SPECT/CT dynamic image quantitative reconstruction and an absolute quantization of myocardial blood flow.

2. Description of Related Art

According to statistics, heart-related diseases account for the death of 192 people per 100,000 population in USA in 2015. Clinically, the technique of nuclear medicine myocardial perfusion single photon emission computed tomography (SPECT) has been accepted as a non-invasive clinical tool capable of effectively inspecting cardiovascular diseases. However, due to the methodology adopted for myocardial perfusion imaging, conventional myocardial perfusion imaging technologies only serve for qualitative image interpretation to detect cardiovascular diseases, and are not yet adapted for quantization of the myocardial blood flow equivalent to that of positron emission tomography (PET). Thus, it is difficult to further improve the accuracy of the inspection on cardiovascular diseases by the nuclear medicine SPECT.

In recent years, various novel multi-pinhole collimators are invented for nuclear medicine SPECT imaging. Examples of such combination include the conventional NaI (Tl) crystal SPECT camera adopting novel multi-pinhole collimators or a novel Cadmium Zinc Telluride (CZT) SPECT semiconductor camera integrated with multi-pinhole collimators. The heart imaging methodologies of these novel devices are advantageous over the conventional SPECT camera with a parallel aperture collimator in terms of the following: (1) the position of gantry is fixed during imaging of the heart, and the tomography is carried out without making the gantry of SPECT rotate with respect to the patient, so the performance and stability of photon detection is increased; (2) the multi-pinhole SPECT facilitates dynamic SPECT data collection and is thus able to provide more accurate data of the dynamic distribution of a heart imaging tracer in the heart area, so an absolute quantization of myocardial blood flow becomes enabled. However, since the imaging geometric structure in the multi-pinhole camera is more complicated, it is more difficult to accurately perform image corrections for the dynamic SPECT data after the data are affected by physical interferences (such as tissue attenuation, photon scatter, collimator blurring, image noises, geometry distortion, and data truncation). Thus, it is still challenging to further generate a dynamic quantitative image with sufficient accuracy for the absolute quantization of myocardial blood flow comparable to the positron emission tomography. Due to the limitations, although the multi-pinhole SPECT camera has the advantage in obtaining the dynamic SPECT data, currently its clinical applicability does not differ significantly from that of the conventional SPECT with a parallel aperture collimator. Thus, if the physical interferences can be corrected effectively, the practical applicability of the multi-pinhole SPECT camera may keep up with that of PET, and the clinical application of myocardial blood flow quantification with the multi-pinhole SPECT camera can be facilitated extensively.

In view of the above, it requires additional work to develop a method for quantitative reconstruction of the multi-pinhole SPECT dynamic image and an absolute quantification for the myocardial blood flow, so as to cavy out an absolute measurement on the myocardial blood flow equivalent to PET and apply the result of the absolute measurement on the myocardial blood flow to the myocardial blood flow condition evaluation.

SUMMARY OF THE INVENTION

An embodiment of the invention provides a quantitative method for nuclear medicine heart image. The method is adapted to carry out a quantitative reconstruction of a multi-pinhole single-photon emission computed tomography (SPECT) or SPECT/CT image and an absolute quantization of myocardial blood flow. The method includes carrying out an iterative image reconstruction, a pixel value conversion, a quantitative myocardial blood flow calculation, and a blood flow condition evaluation. In the iterative image reconstruction, an original projection image is obtained, and iteration is carried out to obtain an SPECT reconstructed image based on the original projection image. The iterative image reconstruction includes the following: carrying out a geometry distortion correction, wherein a plurality of normal rays are translated and a first coordinate conversion calculation is performed through a forward projection and a back projection based on a geometric position of a pinhole and a detector corresponding to the center of the SPECT reconstructed image, so as to obtain correct positions of an oblique ray at the detector and the SPECT reconstructed image and correct a geometry distortion in the SPECT reconstructed image resulting from the oblique ray; carrying out a data truncation compensation, wherein a truncated area in a field of view of the original projection image is calculated by expanding a field of view of the SPECT reconstructed image and performing another front projection, a count of a truncated area in an image projected from the SPECT reconstructed image is combined with the original projection image to expand a field of view of the original projection image, and iteration is performed with the original projection image having an expanded field of view as an input to expand the field of view of the SPECT reconstructed image until convergence is reached, so as to correct an artifact resulting from a data truncation in the SPECT reconstructed image; carrying out a tissue attenuation correction, wherein a tissue attenuation matrix is established by calculating an attenuation value of each ray from the pinhole to the detector based on a tissue attenuation diagram, and underestimation of a marker imaging tracer extraction activity of a heart and marker imaging tracer extraction activities of parts other than the heart caused by tissue attenuation are corrected based on the tissue attenuation matrix, so as to correct the tissue attenuation in the SPECT reconstructed image; carrying out an image space resolution recovery, wherein a distance between a pixel of the SPECT reconstructed image and the pinhole is calculated based on a ray passing through the pinhole from the detector to the SPECT reconstructed image and a trajectory of the ray, a spread function matrix is established based on the distance between the pixel and the pinhole, and iteration is carried out based on the spread function matrix to recover a space resolution during imaging of the pinhole; and carrying out a noise removal, wherein noises in the SPECT reconstructed image are removed through iteration with a filter. Then, a pixel value conversion is carried out, wherein the SPECT reconstructed image is converted based on a linear relation between a pixel value and an absolute activity concentration of the marker imaging tracer, so as to turn each pixel value of the SPECT reconstructed image into a unit with a physical meaning to obtain a quantitative SPECT image. Subsequently, a quantitative myocardial blood flow calculation is carried out, wherein activities at a blood pool and a myocardium are measured dynamically based on the quantitative SPECT image, so as to obtain a blood pool time activity curve and a myocardial time activity curve, a first dynamic parameter is obtained through fitting the blood pool time activity curve and the myocardial time activity curve to an one-tissue compartment physiological mathematical model, a first rate of the marker imaging tracer entering a myocardial cell is obtained based on the first dynamic parameter, and an absolute blood flow value of the myocardium is obtained by converting the first dynamic parameter based on an extraction fraction of the marker imaging tracer. Then, a blood flow condition evaluation is carried out, wherein a plurality of indicators are obtained based on the first rate to establish a blood flow condition diagram having a blood flow condition, and an evaluation is carried out based on the blood flow condition diagram to output a blood flow condition evaluation result.

According to an embodiment of the invention, the method further includes: carrying out a radionuclide physical decay correction, wherein before the iterative image reconstruction, a radionuclide decay correction coefficient at each dynamic time point in a dynamic SPECT collection is calculated based on a time point of starting the dynamic SPECT collection, a duration of the collection, and a half-life of the marker imaging tracer and a radioactive count in the original projection image is corrected based on the radionuclide decay correction coefficient.

According to an embodiment, the method further includes: carrying out a scatter correction, wherein a scatter component in the original projection image is calculated based on a scatter energy window before the iterative image reconstruction, and the scatter component is subtracted from the original projection image to obtain the original projection image after the scatter correction.

According to an embodiment of the invention, the method further includes: carrying out an intra-scan patient movement correction, wherein after the iterative image reconstruction, based on the quantitative SPECT image at each dynamic time point and using the center of the heart as an origin, a second coordinate conversion, a ray tracing, and a geometric shape approximation are carried out to find boundaries of the blood pool and the myocardium, and a vector for correcting a movement of a patient is obtained based on a maximum correlation, and the quantitative SPECT image is corrected.

According to an embodiment of the invention, the intra-scan patient movement correction further includes: converting the quantitative SPECT image from a Cartesian coordinate system to a spherical coordinate system through the second coordinate conversion, and converting the boundary of the myocardium from the spherical coordinate system back to the Cartesian coordinate system; approximating the heart to a geometric shape by performing the geometric shape approximation; and using a position of the myocardium at the last dynamic time point as the reference, moving a position of the blood pool to calculate the maximum correlation between the position of the myocardium and the position of the blood pool.

According to an embodiment of the invention, the geometry distortion correction further includes: respectively converting a normal ray passing through the pinhole and forward-facing the SPECT reconstructed image and a normal back ray forward-facing the detector into an oblique ray and an oblique back ray through the translation and the first coordinate conversion calculation based on the forward projection and the back projection, so as to obtain a correct position of the oblique ray at the detector and a correct position of the oblique back ray at the SPECT reconstructed image.

According to an embodiment of the invention, wherein the tissue attenuation correction further includes: obtaining an 140 keV attenuation coefficient of each pixel in the SPECT reconstructed image based on the tissue attenuation diagram, and calculating an attenuation value of the pixel in the SPECT reconstructed image corresponding to the detector with an exponential model and a linear integration based on a position of the SPECT reconstructed image corresponding to the pinhole and the detector to establish the tissue attenuation matrix.

According to an embodiment of the invention, the image space resolution recovery further includes: considering the pinhole as a disc or having a geometrically symmetrical shape, calculating a distance between the pixel of the SPECT reconstructed image and the pinhole based on a common center of a plurality of rays passing through the pinhole from the detector to the SPECT reconstructed image and trajectories of the rays, and calculating a range and an area covered through spreading with distance based on a solid angle of the pinhole, so as to calculate the spreading coefficient matrix related to distances of the rays with respect to the disc.

According to an embodiment of the invention, the noise removal further includes: carrying out iteration based on an analytic filter or a wavelet filter to remove the noises in the SPECT reconstructed image, and comparing the original projection image after filtering and a front projection image after filtering during the iteration to filter out noises, wherein the wavelet filter performs basis expansion on an image in a stationary mode, excludes a high-frequency expansion of coefficients with a fixed window in a histogram of expansion coefficients of different orders, and removes the noises in the SPECT reconstructed image by carrying out filtering the expansion coefficients with an analytic function.

According to an embodiment of the invention, the blood flow condition evaluation includes: conducting an absolute quantization of myocardial blood flow based on the quantitative SPECT image, establishing the blood flow condition diagram with markings of different colors is established based on the indicators of rest flow, stress flow and myocardial flow reserve values measured from a group of people.

According to an embodiment of the invention, the indicators in the blood flow condition evaluation include a stress flow, a rest flow, and a myocardial flow reserve.

According to an embodiment, the quantitative myocardial blood flow calculation further includes: obtaining a second dynamic parameter and a third dynamic parameter through fitting the blood pool time activity curve and the myocardial time activity curve to the one-tissue compartment physiological mathematical model, obtaining a second rate of the marker imaging tracer exiting the myocardial cell based on the second dynamic parameter, and obtaining a third rate of the marker imaging tracer functioning with the myocardial cell based on the third dynamic parameter.

An embodiment of the invention provides an electronic device for executing a quantitative method for a nuclear medicine heart image. The electronic device includes a storage storing a plurality of modules and a processor, coupled to the storage and accessing and executing the modules stored in the storage to carry out an iterative image reconstruction, a pixel value conversion, a quantitative myocardial blood flow calculation, and a blood flow condition evaluation. In the iterative image reconstruction, an original projection image is obtained, and iteration is carried out to obtain an SPECT reconstructed image based on the original projection image. The iterative image reconstruction includes the following: a geometry distortion correction, wherein a plurality of normal rays are translated and a first coordinate conversion calculation is performed through a forward projection and a back projection based on a geometric position of a pinhole and a detector corresponding to the center of the SPECT reconstructed image, so as to obtain correct positions of an oblique ray at the detector and the SPECT reconstructed image and correct a geometry distortion in the SPECT reconstructed image resulting from the oblique ray; a data truncation compensation, wherein a truncated area in a field of view of the original projection image is calculated by expanding a field of view of the SPECT reconstructed image and performing a front projection, a count of a truncated area in an image projected from the SPECT reconstructed image is combined with the original projection image to expand a field of view of the original projection image, and iteration is performed with the original projection image having an expanded field of view as an input to expand the field of view of the SPECT reconstructed image until convergence is reached, so as to correct an artifact resulting from a data truncation in the SPECT reconstructed image; a tissue attenuation correction, wherein a tissue attenuation matrix is established by calculating an attenuation value of each ray from the pinhole to the detector based on a tissue attenuation diagram, and underestimation of a marker imaging tracer extraction activity of a heart and marker imaging tracer extraction activities of parts other than the heart caused by tissue attenuation are corrected based on the tissue attenuation matrix, so as to correct the tissue attenuation in the SPECT reconstructed image; an image space resolution recovery, wherein a distance between a pixel of the SPECT reconstructed image and the pinhole is calculated based on a ray passing through the pinhole from the detector to the SPECT reconstructed image and a trajectory of the ray, a spread function matrix is established based on the distance between the pixel and the pinhole, and iteration is carried out based on the spread function matrix to recover a space resolution during imaging of the pinhole; and a noise removal, wherein noises in the SPECT reconstructed image are removed through iteration with a filter. Then, in the pixel value conversion, the SPECT reconstructed image is converted based on a linear relation between a pixel value and an absolute activity concentration of the marker imaging tracer, so as to turn each pixel value of the SPECT reconstructed image into a unit with a physical meaning to obtain a quantitative SPECT image. In the quantitative myocardial blood flow calculation, activities at a blood pool and a myocardium are measured dynamically based on the quantitative SPECT image, so as to obtain a blood pool time activity curve and a myocardial time activity curve, a first dynamic parameter is obtained through fitting the blood pool time activity curve and the myocardial time activity curve to an one-tissue compartment physiological mathematical model, a first rate of the marker imaging tracer entering a myocardial cell is obtained based on the first dynamic parameter, and an absolute blood flow value of the myocardium is obtained by converting the first dynamic parameter based on an extraction fraction of the marker imaging tracer. In the blood flow condition evaluation, wherein a plurality of indicators are obtained based on the first rate to establish a blood flow condition diagram having a blood flow condition, and an evaluation is carried out based on the blood flow condition diagram to output a blood flow condition evaluation result.

Based on the above, the quantitative method for the nuclear medicine heart image according to the embodiments of the invention is able to remove the respective physical interferences in the dynamic SPECT images, so as to obtain the quantitative image (unit of pixel value: Bq/ml) equivalent to PET. Accordingly, the absolute quantization of myocardial blood flow is able to be calculated based on the methodology equivalent to that of PET. Therefore, quantification of myocardial blood flow may serve in the myocardial blood flow condition evaluation.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

FIGS. 12A and 12B are flowcharts illustrating a quantitative method for a nuclear medicine heart image according to an embodiment of the invention.

Figure 1:
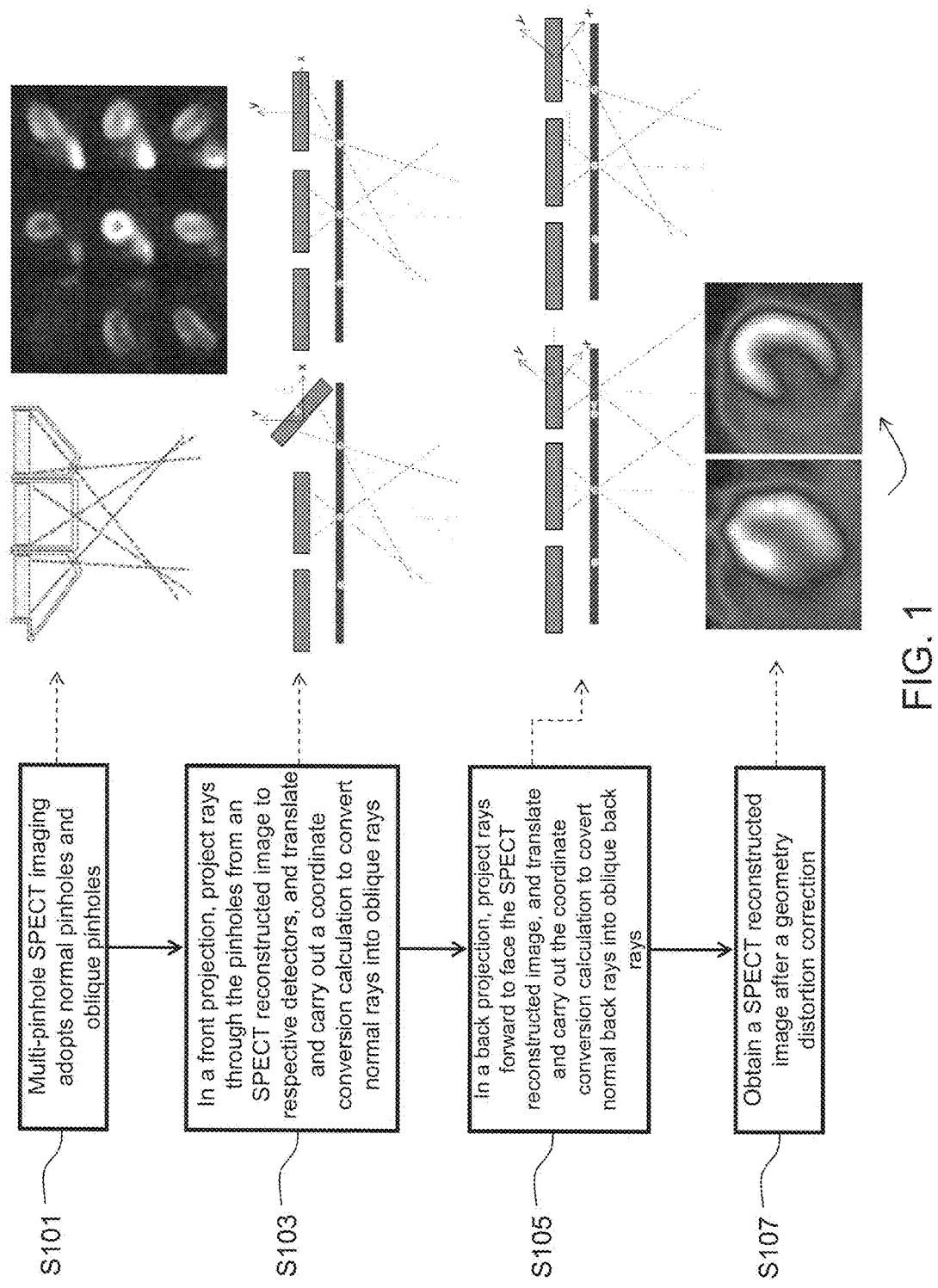
FIG. 1 is a flowchart illustrating a geometry distortion correction in an iterative image reconstruction according to an embodiment of the invention.

In order to make the aforementioned and other features and advantages of the invention comprehensible, several exemplary embodiments accompanied with figures are described in detail below.

DESCRIPTION OF THE EMBODIMENTS

Reference will now be made in detail to the present preferred embodiments of the invention, examples of which are illustrated in the accompanying drawings. Wherever possible, the same reference numbers are used in the drawings and the description to refer to the same or like parts.

The invention provides a quantitative method for a nuclear medicine heart image and an electronic device using the same, and is adapted to carry out a quantitative reconstruction of a multi-pinhole single-photon emission computed tomography (SPECT) or SPECT/CT image and an absolute quantization of myocardial blood flow and evaluate a myocardial blood flow condition. Particularly, a thorough correction is essential to obtain the quantitative SPECT image and the absolute quantization of myocardial blood flow. Besides, such through correction effectively increases an image quality. A quantitative method for a nuclear medicine heart image according to an embodiment of the invention includes a plurality of steps as explicated in the following.

First of all, a radionuclide physical decay correction is carried out. For a SPECT or SPECT/CT apparatus with a multi-pinhole collimator, based on a time point of starting a dynamic SPECT collection, a duration of the collection, and a half-life of a 99mTC marker imaging tracer, a decay correction coefficient of the 99mTC marker imaging tracer at respective dynamic time points in the SPECT collection is calculated with an exponential decay model, and a radioactive count in an original projection image is corrected based on the radionuclide decay correction coefficient.

Then, a scatter correction is carried out. Before photons of a main peak reaches a detector, the photons may pass through body tissues and thus be scattered. Scatter may result in overestimation on heart extraction and activities of parts other than the heart in an SPECT reconstructed image. Thus, the original projection image with a main peak energy window (140±10% keV or 126-154 keV) and a scattered image with a scatter energy window (118±12% keV or 110-125 keV) may be adopted, and a scatter component in the original projection image is estimated based on a triangle-like relation between the scatter component and the main peak energy window. Then, the scatter correction is carried out by subtracting the scatter component from the original projection image to obtain the original projection image after the scatter correction.

After the radionuclide physical decay correction and the scatter correction, the iterative image reconstruction is carried out. The corrected original projection image is used in the iterative image reconstruction, and iteration is carried out to obtain an SPECT reconstructed image. In the exemplary embodiment, the iterative image reconstruction includes a geometry distortion correction, data truncation compensation, a tissue attenuation correction, an image space resolution recovery, and a noise removal. Details of the iterative image reconstruction will be described in the following.

Regarding the geometry distortion correction, FIG. 1 is a flowchart illustrating a geometry distortion correction in an iterative image reconstruction according to an embodiment of the invention. Referring to FIG. 1, multi-pinhole SPECT imaging adopts normal pinholes and oblique pinholes (Step S101). Based on a geometric position of each of the pinholes and detectors corresponding to the center of the SPECT reconstructed image, a ray (also referred to as a normal ray) is adopted for projection in a front projection operation during the iteration. The ray may travel to the respective detector through the pinhole. All the rays of the SPECT reconstructed image are firstly projected to forward-face the detectors. Then, based on actual angles and positions of the oblique detectors, a translation and a coordinate conversion computation (also referred to as "first coordinate conversion computation") are carried out to convert the normal rays into oblique rays to position (or obtain) the oblique rays at correct positions on the detectors (Step S103). Similarly, in a back projection, a ray (also referred to as a normal back ray) is projected forward to face the SPECT reconstructed image. Then, based on actual angles and positions when the oblique detectors and pinholes face the SPECT reconstructed image in an oblique direction, the translation and the coordinate conversion computation (also referred to as "first coordinate conversion computation) convert the normal back ray into an oblique back rays (Step S105), so as to position (or obtain) correct positions of the oblique back ray on the SPECT reconstructed image. Hence, a geometry distortion in the SPECT reconstructed image resulting from an incorrect position of the oblique ray is corrected, and the SPECT reconstructed image after the geometry distortion correction is obtained (Step S107).

Figure 2:
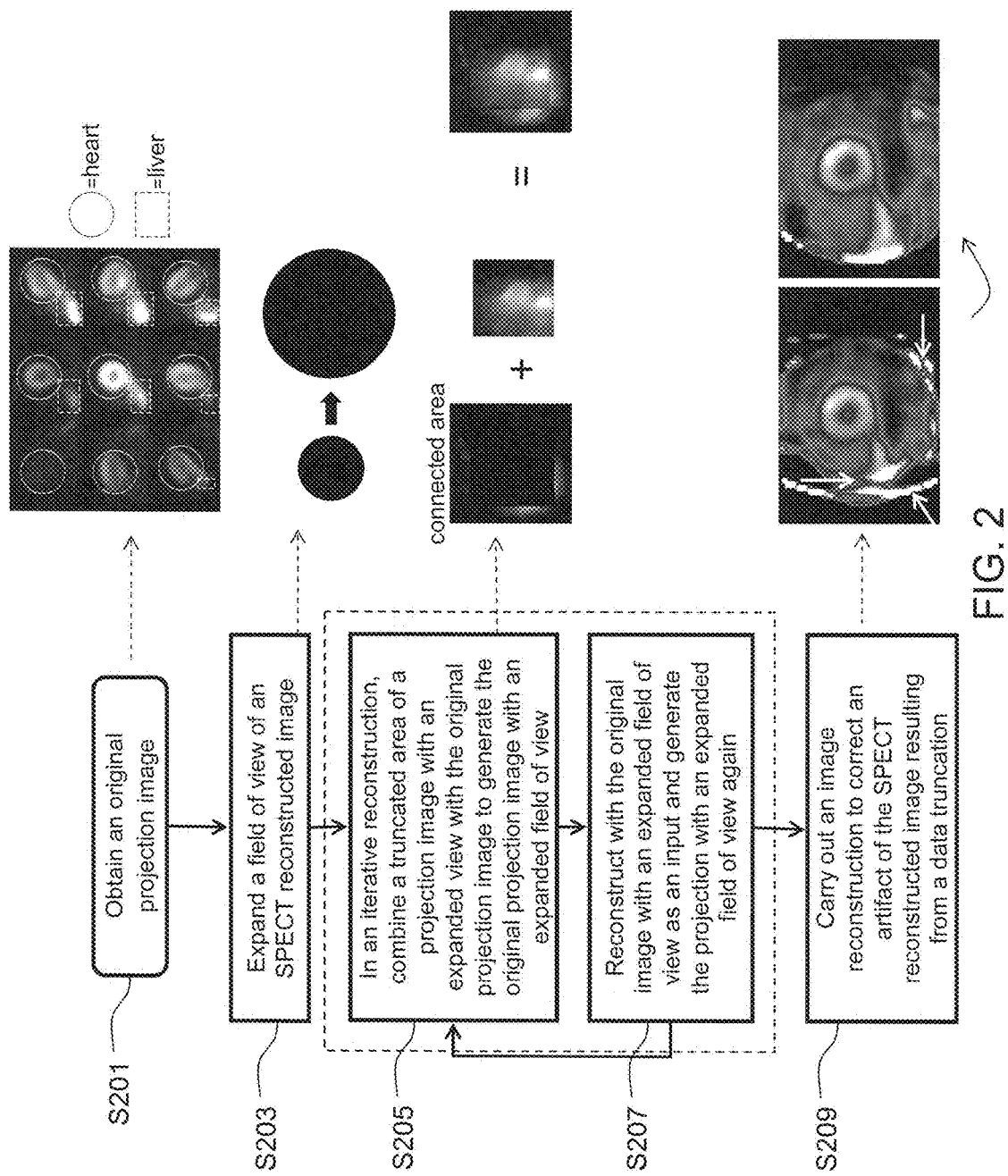
FIG. 2 is a flowchart illustrating data truncation compensation in an iterative image reconstruction according to an embodiment of the invention.

Regarding the compensation for data truncation, FIG. 2 is a flowchart illustrating a data truncation compensation in an iterative image reconstruction according to an embodiment of the invention. Since pinhole imaging is known for a smaller field of view in an image, in addition to including the heart in the field of view of the pinhole, it is normal that other organs (e.g., lung, liver, and intestinal tract) are partially included or excluded in the field of view of the pinhole, thus resulting in a data truncation. Therefore, an inconsistency in counts of a non-heart organ among pinhole images at the respective angles may arise. Hence, an artifact may be generated on a periphery of the SPECT reconstructed image. It should be noted that, when the artifact is near the heart, the accuracy of a heart image is affected. During the data truncation compensation, the original projection image is obtained and adopted (Step S201). In reconstruction of the SPECT image, fields of view of all the original projection images are covered to expand the field of view of the SPECT reconstructed image (Step S203). Then, the SPECT reconstructed image with the expanded field of view is projected (namely, a projection operation is carried out) to the detector to estimate a truncated area in the field of view of the original projection image. At respective front projections, the SPECT reconstructed image with the expanded field of view is firstly projected to obtain a projection image with an expanded field of view. Then, the counts in the truncated area of the projection image is combined (or connected) with the original projection images to expand the field of views of the original projection images (Step S205). Through iteration, the original projection image with an expanded field of view is input (Step S207) to expand the field of view of the SPECT reconstructed image until convergence is reached, so as to correct the artifact resulting from the data truncation (Step S209).

Figure 3:
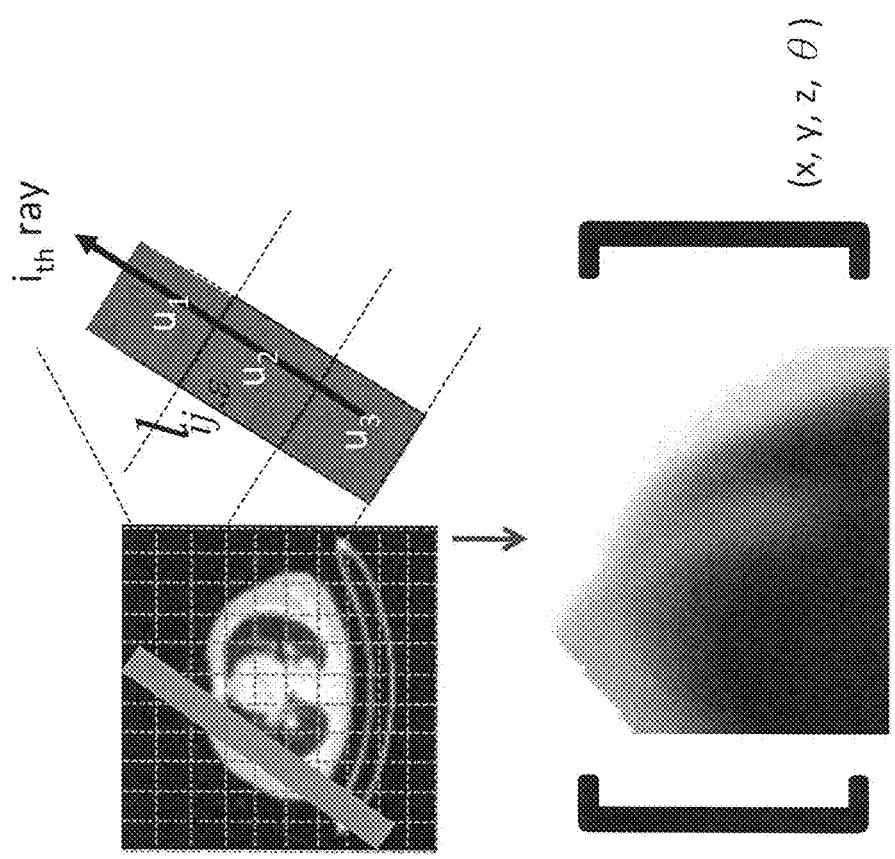
FIG. 3 is a schematic view illustrating generation of a tissue attenuation matrix according to an embodiment of the invention.

Regarding the tissue attenuation correction, FIG. 3 is a schematic view illustrating generation of a tissue attenuation matrix according to an embodiment of the invention. Referring to FIG. 3, a CT image is converted into a tissue attenuation diagram. Based on the tissue attenuation diagram, a 140 keV attenuation coefficient of each pixel in the SPECT reconstructed image is obtained. Based on a position of the SPECT reconstructed image corresponding to the detector of the pinhole, an exponential model and a linear integration are adopted to calculate an attenuation value of each pixel unit of the SPECT reconstructed image corresponding to a ray emitted from the pinhole to the detector, thereby establishing a tissue attenuation matrix. In the iterative reconstruction, the tissue attenuation matrix serves to correct underestimation on a marker imaging tracer extraction activity of the heart and marker imaging tracer extraction activities of parts other than the heart caused by tissue attenuation, so as to correct the tissue attenuation in the SPECT reconstructed image. In addition, the tissue attenuation matrix records an extent to which photons of each corresponding ray attenuate with four parameters (x, y, z, θ). An accurate alignment of CT and SPECT data is required before the tissue attenuation correction is carried out, so as to increase the accuracy of the tissue attenuation correction.

Regarding the image space resolution recovery, based on a geometric size of an aperture of each pinhole and a geometric position of each pinhole aperture corresponding to an image center, the pinhole is considered as a disc or having a geometrically symmetrical shape. A distance between the pixel of the SPECT reconstructed image and the pinhole is calculated based on a center and a trajectory of each ray passing through the pinhole from the detector to the SPECT reconstructed image. Based on the distance between the pixel and the pinhole and a solid angle of the pinhole, a range and an area covered through spreading with distance is calculated, so as to calculate a spread function matrix relating to a distance of each ray and the pinhole disc. The spread function matrix is adopted in the iterative image reconstruction to recover a space resolution of pinhole imaging.

Regarding the noise removal, in the iterative image reconstruction, an analytic filter or a wavelet filter may serve to remove noises in the SPECT reconstructed image. During the iteration, an original image after filtering and the front projection image after filtering are compared to filter out the noises. As an alternative, the wavelet filter may also be adopted for the noises of the original image and the front projection image during the iterative reconstruction. Similarly, during the iteration, the original image after filtering and the front projection image after filtering are compared to filter out the noises. The wavelet filter may carry out a basis expansion on an image in a stationary mode, excludes a high-frequency expansion coefficient using a fixed window width in a histogram of expansion coefficients of different orders, filters the expansion coefficients with an analytic function, and removes the noises in the SPECT reconstructed image by carrying out filtering the expansion coefficients with an analytic function.

Regarding pixel value conversion, after the respective physical image corrections in the iterative image reconstruction, based on a linear relation between a pixel value and an absolute 99mTc activity concentration (i.e., an absolute activity concentration of the marker imaging tracer), the SPECT reconstructed image is converted to turn each pixel value of the SPECT reconstructed image into a unit with a physically meaning (Bq/ml), thereby obtaining a quantitative SPECT image. The linear relation between the pixel value and the absolute 99mTc activity concentration may be obtained by filling a known 99mTc activity concentration into a phantom and performing multiple times of data collection, image reconstruction and data analysis during the decay of 99mTc.

Figure 4D:
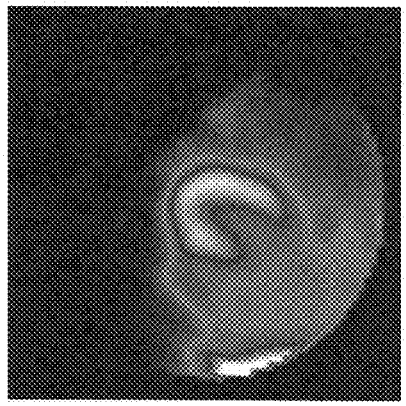
FIGS. 4A to 4G are views illustrating influences of physical correction on SPECT reconstructed images and pixel values according to an embodiment of the invention.
Figure 4C:
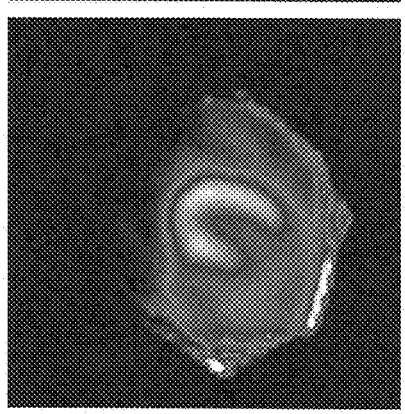
Figure 4G:
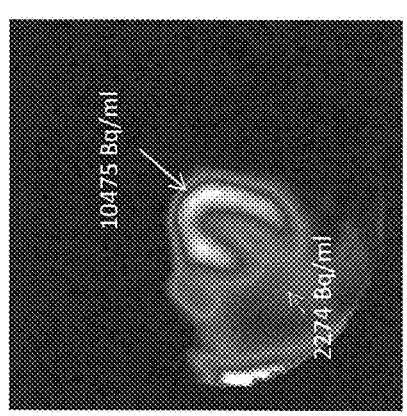
Figure 4B:
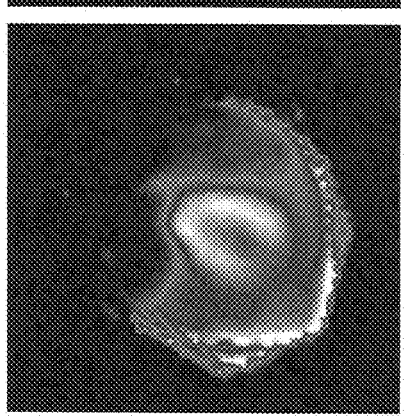
Figure 4F:
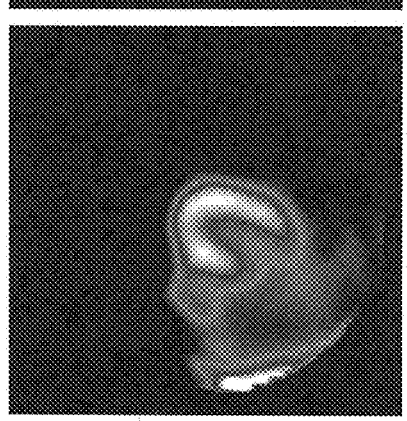
Figure 4A:
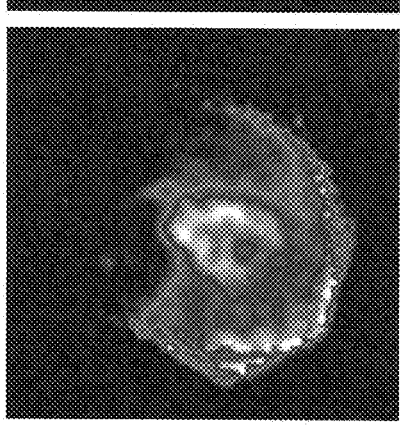
Figure 4E:
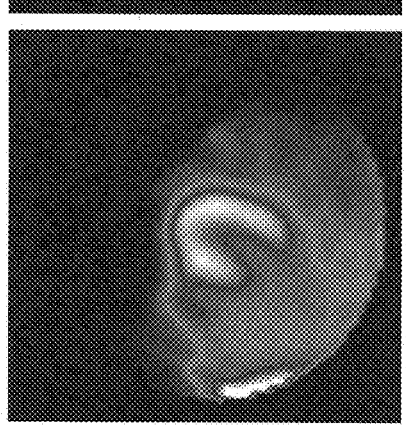
Figure 5:
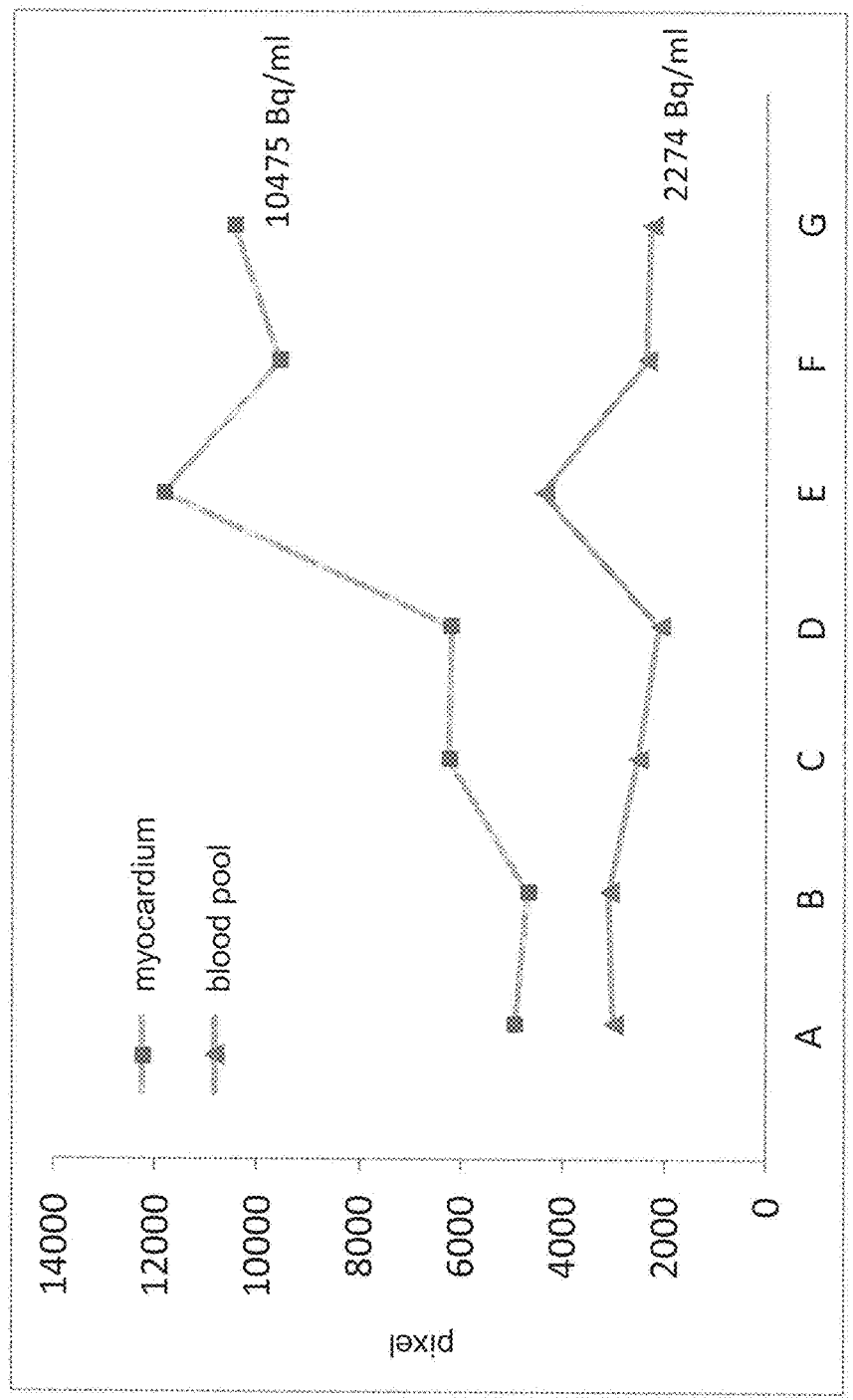
FIG. 5 is a diagram illustrating a measurement on pixel values of a blood pool and a myocardium according to an embodiment of the invention.

FIGS. 4A to 4G are views illustrating influences of physical correction on SPECT reconstructed images and pixel values according to an embodiment of the invention. FIG. 4A illustrates an image without the respective physical image corrections in the iterative image reconstruction. The image shown in FIG. 4A has more noises and the heart image is distorted. FIG. 4B illustrates an image after the noise removal. The image of FIG. 4B shows that the noises in the image are effectively removed. FIG. 4C illustrates an image after the noise removal and the geometry distortion correction. The image of FIG. 4C shows that the geometry distortion in the heart image is effectively corrected, and pixel values of the myocardium are increased while pixel values of the blood pool are decreased. FIG. 4D illustrates an image after the noise removal, the geometry distortion correction and the data truncation compensation. The image of FIG. 4D shows that the artifact resulting from data truncation is effectively removed, so the pixel values of the blood pool are decreased. FIG. 4E illustrates an image after the noise removal, the geometry distortion correction, the data truncation compensation, and the tissue attenuation correction. The heart image shown in FIG. 4E is more uniform, the pixel values of the myocardium and the blood pool are increased by multiple times, the underestimation on the extraction value of the myocardium and the activity of the blood pool resulting from tissue attenuation is consequently corrected. FIG. 4F illustrates an image after the noise removal, the geometry distortion correction, the data truncation compensation, the tissue attenuation correction, and the scatter correction. The image of FIG. 4F shows an increased image contrast, and the overestimation on the activities of the myocardium and the blood pool resulting from scatter is consequently reduced. FIG. 4G illustrates an image after the noise removal, the geometry distortion correction, the data truncation compensation, the tissue attenuation correction, the scatter correction, the space resolution correction, and the radionuclide physical decay correction. The image of FIG. 4G shows that the image contrast and resolution are further increased, an overall image quality is significantly improved, and the image is converted from a non-quantitative format into a quantitative format (unit of pixel value: Bq/ml). According to FIG. 4G, a blood pool activity of 2274 Bq/ml and a myocardium extraction activity of 10475 Bq/ml are rendered. Besides, FIG. 5 is a diagram illustrating a measurement on pixel values of a blood pool and a myocardium according to an embodiment of the invention. FIG. 5 shows corresponding pixel values of the blood pool and the myocardium corresponding to FIGS. 4A to 4H. In addition, the unit of the pixel in FIG. 5 is Bq/ml.

Figure 6:
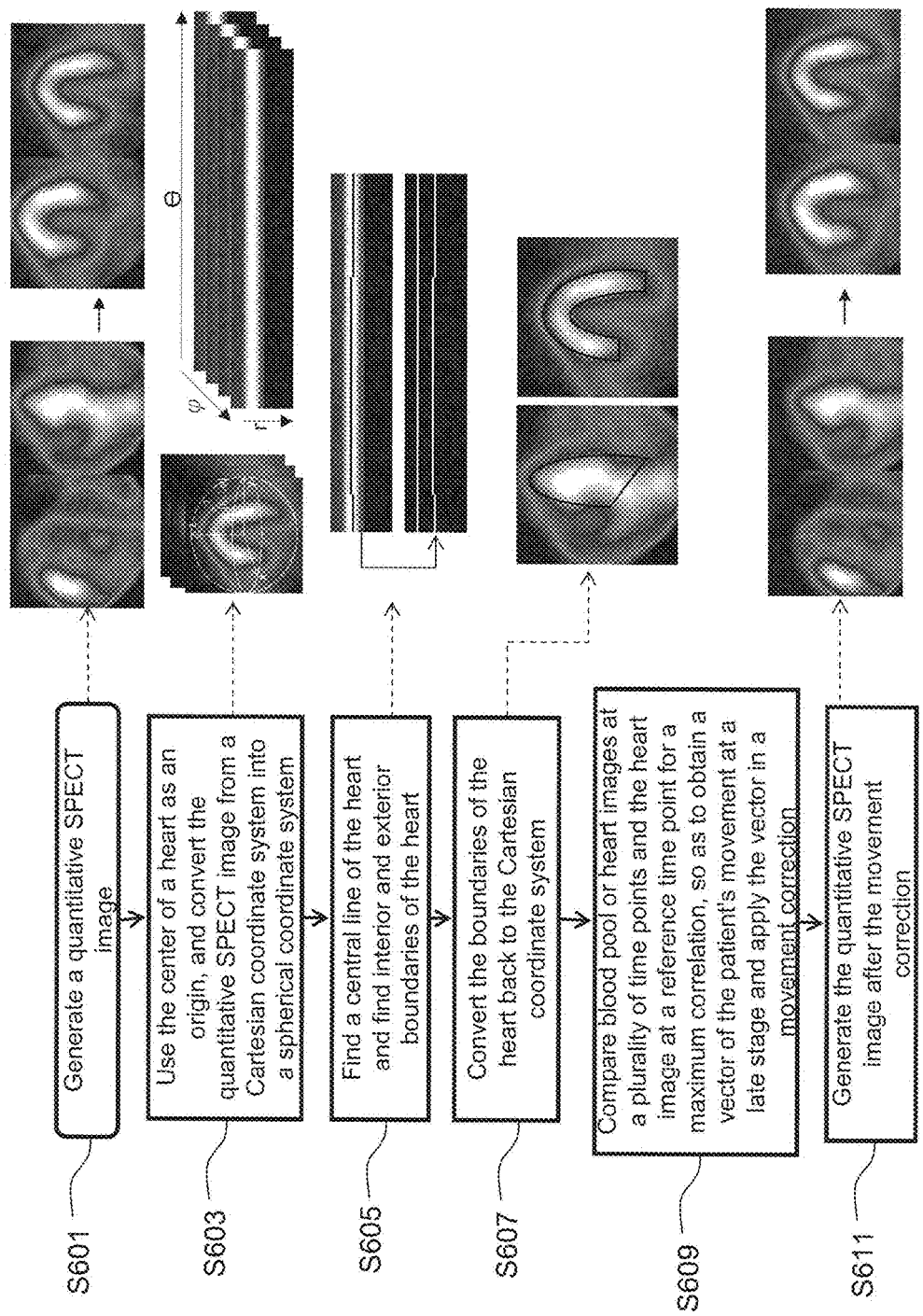
FIG. 6 is a flowchart illustrating an intra-scan patient movement correction according to an embodiment of the invention.

Regarding an intra-scan patient movement correction, FIG. 6 is a flowchart illustrating an intra-scan patient movement correction according to an embodiment of the invention. Referring to FIG. 6, the intra-scan patient movement correction is carried out to correct a change of a heart position resulting from an excessive respiratory amplitude or a body movement of the patient. The change of the heart position may affect the accuracy of quantization of the image and the myocardial blood flow. After the iterative image reconstruction, a quantitative SPECT image may be generated after reconstructing the patient's dynamic data (Step S601). Using the center of the heart as an origin, the quantitative SPECT images at the respective dynamic time points are converted from a Cartesian coordinate system into a spherical coordinate system (also referred to as second coordinate conversion, Step S603). A boundary of the blood pool is found through ray tracing in images of the blood pool at earlier dynamic frames. In addition, a position of a central line of the heart is also found through ray tracing in an image of the heart at later stage. In addition, a distance from the central line to a boundary of the heart is calculated to obtain a boundary of the myocardium (Step S605). Then, the boundaries of the blood pool and the myocardium are converted from the spherical coordinate system back to the Cartesian coordinate system, and the heart is approximated to an elliptical sphere or other shapes similar to the geometric shape of the heart. Using a position of the myocardium at the last dynamic time point as the reference, a maximum correlation between an earlier-stage position of the blood pool and the reference position of the myocardium is calculated, so as to obtain a vector of the patient's movement at an earlier stage. A maximum correlation between a later-stage position of the heart and the reference position of the heart is calculated, so as to obtain a vector of the patient's movement at a late stage. Vectors at earlier and late stages are utilized to automatically correct the patient's movement (Step S609). Lastly, the quantitative SPECT image after the movement correction is generated based on the vectors.

Figure 7:
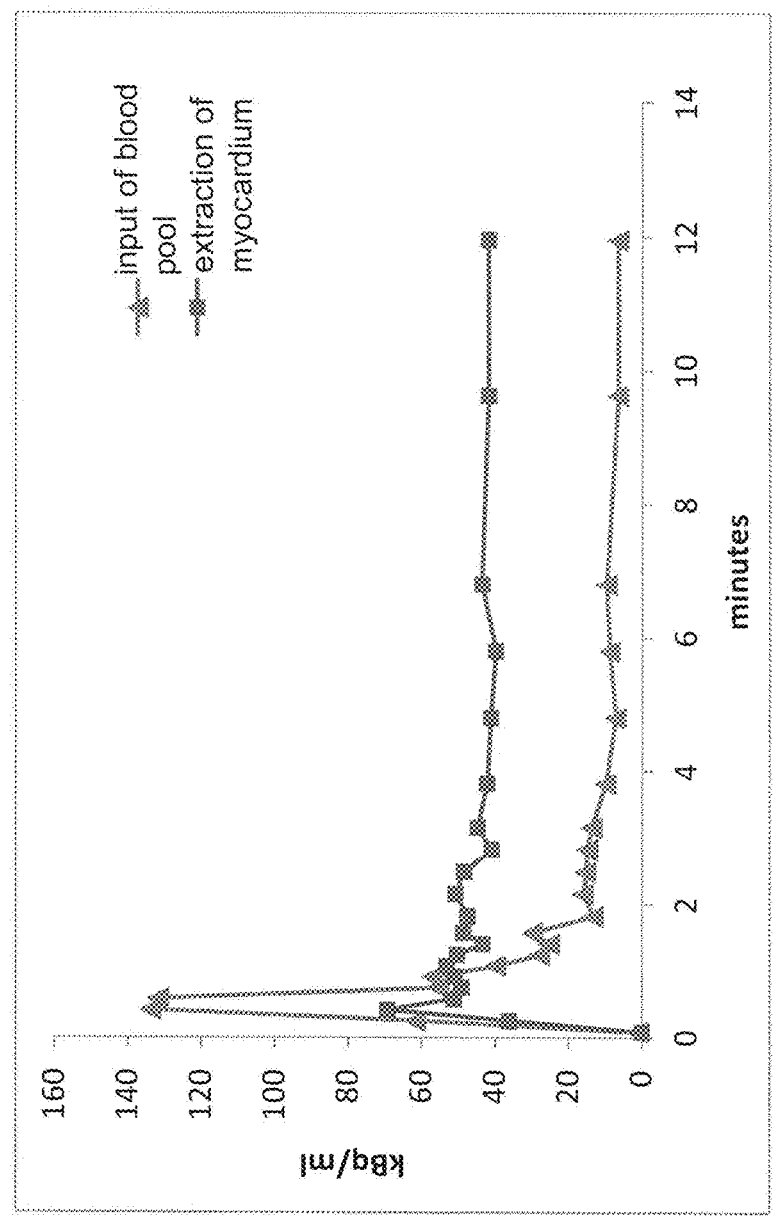
FIG. 7 is a diagram illustrating a blood pool activity curve and a myocardial activity curve obtained from a quantitative multi-pinhole dynamic SPECT image.
Figure 7:
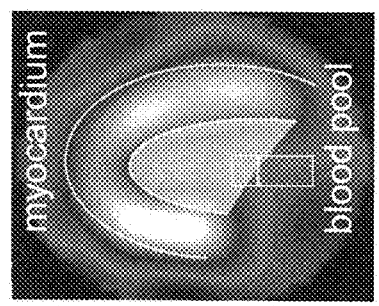

Regarding a quantitative myocardial blood flow calculation, based on the multi-pinhole dynamic SPECT data, the image is processed through the respective physical corrections. In addition, based on the quantitative SPECT image, dynamic activity measurements at the blood pool and the myocardium (unit: Bq/ml) are performed to obtain a blood pool time activity curve and a myocardial time activity curve. Then, after fitting the curves to an one-tissue compartment physiological mathematical model, a first dynamic parameter k1 (unit: ml/min/g), a second dynamic parameter k2 (unit: ml/min), and a third dynamic parameter k3 (unit: ml/min) are obtained. Based on the first dynamic parameter k1, a first rate of the marker imaging tracer entering a myocardial cell is obtained. In addition, by converting the first dynamic parameter k1 based on an extraction fraction of the 99mTc marker imaging tracer, an absolute blood flow value is obtained. Based on the second dynamic parameter k2, a second rate of the 99mTc marker imaging tracer exiting the myocardial cell is obtained. Based on the third dynamic parameter k3, a third rate of the 99mTc marker imaging tracer functioning with the myocardial cell is obtained. FIG. 7 is a diagram illustrating a blood pool activity curve and a myocardial activity curve obtained from a quantitative multi-pinhole dynamic SPECT image.

Figure 8:
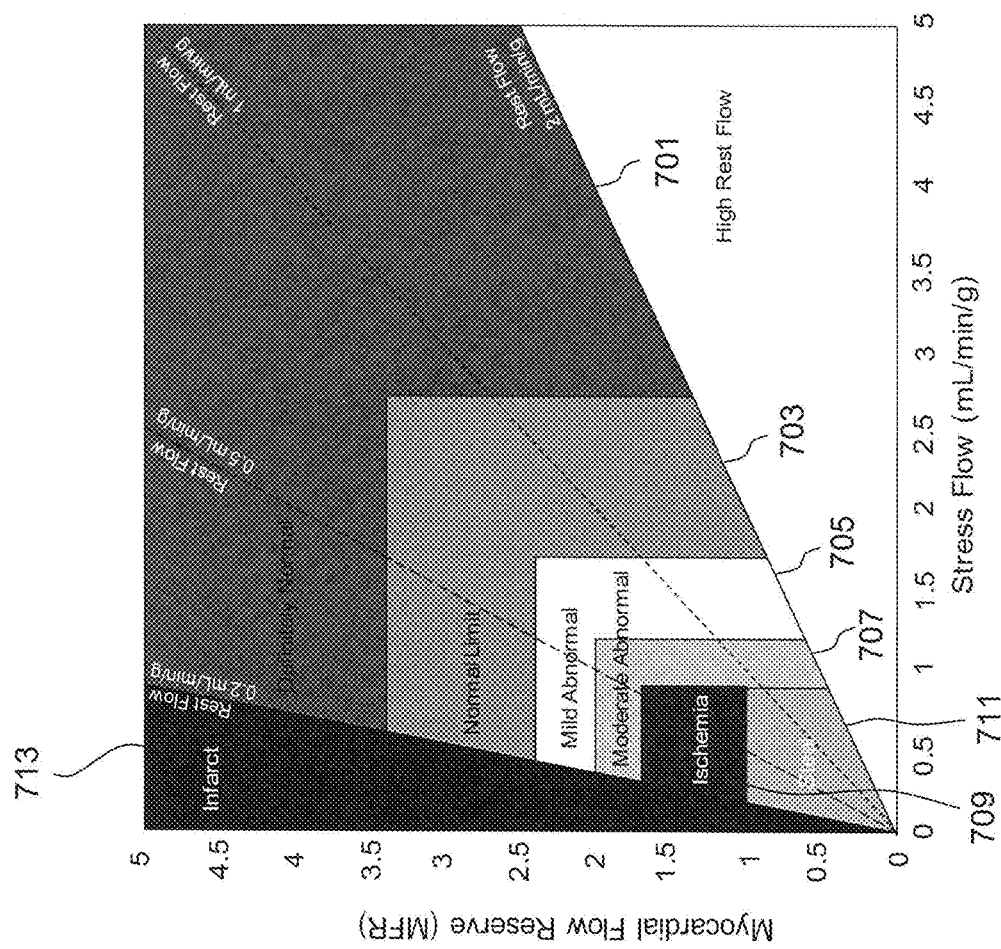
FIG. 8 is a diagram illustrating a blood flow condition constructed based on a stress flow, a rest flow, and a myocardial flow reserve according to an embodiment of the invention.

Regarding a blood flow condition evaluation, an absolute quantization of myocardial blood flow is conducted based on the quantitative SPECT image. By quantizing the blood flow of a human body, three indicators, namely a stress flow (unit: ml/min/g), a rest flow (unit: ml/min/g) and a myocardial flow reserve, are obtained. In addition, a blood flow condition diagram with markings of different colors is established based on a group of people and serves to indicate a blood flow condition. Accordingly, the blood flow condition is evaluated. For example, an evaluation may be carried out based on an absolute blood flow value and the blood flow condition diagram to output a blood flow condition evaluation result. FIG. 8 is a diagram illustrating a blood flow condition constructed based on a stress flow, a rest flow, and a myocardial flow reserve according to an embodiment of the invention. Based on a flow rate of the blood flow, the blood flow condition is divided into an area 701, an area 703, an area 705, an area 707, an area 709, an area 711, and an area 713. In addition, the area 701, the area 703, the area 705, the area 707, the area 709, the area 711, and the area 713 may be respectively marked in red, orange, yellow, green, blue, grey, and black.

EXAMPLE 1

Figure 9:
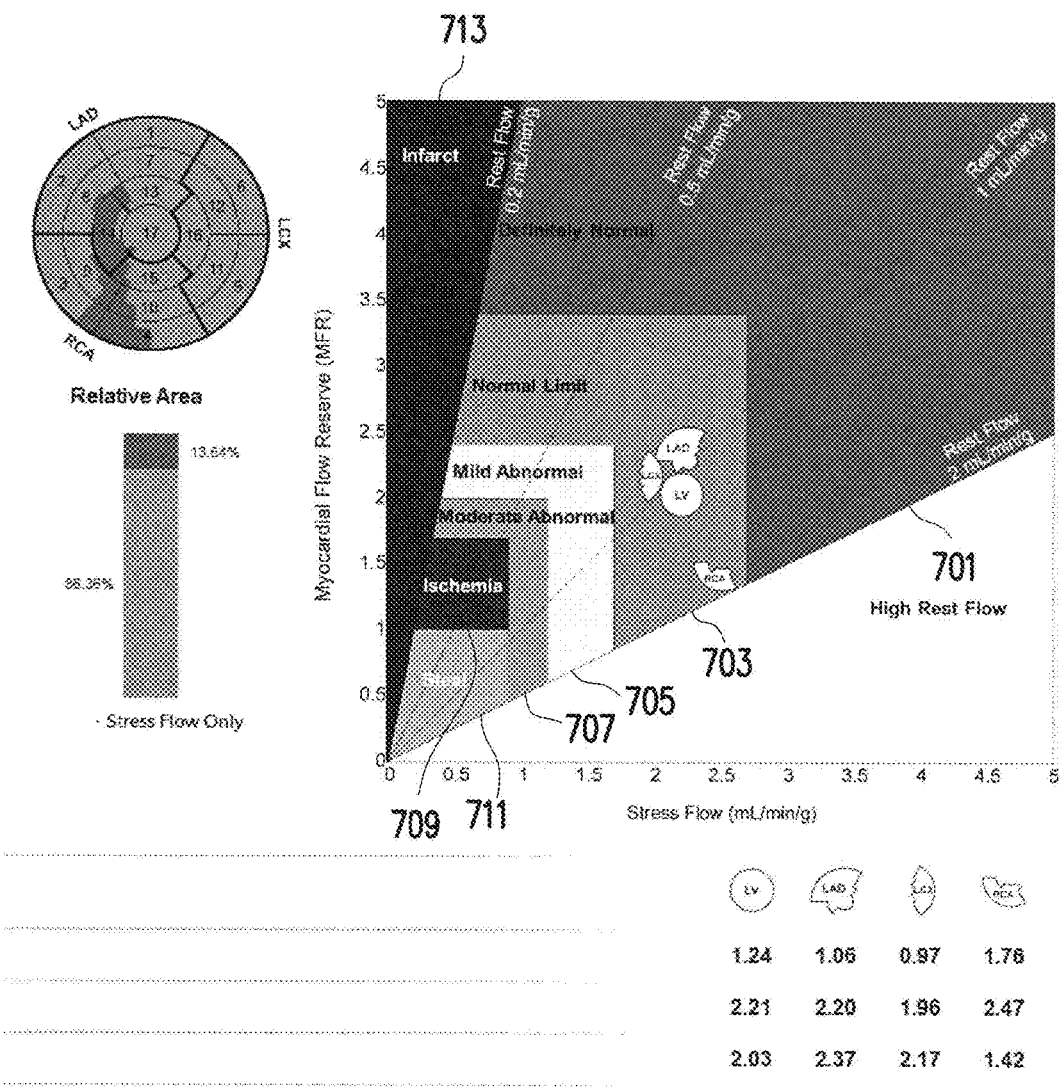
FIG. 9 is a schematic diagram illustrating Example 1 of the invention.

FIG. 9 is a schematic diagram illustrating Example 1 of the invention. FIG. 9 shows a 63-year-old female without a risk of a cardiovascular disease. Through the multi-pinhole dynamic SPECT quantitative image reconstruction, the absolute quantization of myocardial blood flow, and the blood flow condition evaluation according to the method in the embodiment of the invention, it is learned that in the left ventricular (LV) area, the left anterior descending (LAD) area, the left circumflex (LCX) area, and the right coronary artery (RCA) area, the rest flows are respectively 1.24 ml/min/g, 1.06 ml/min/g, 0.97 ml/min/g, and 1.76 ml/min/g, the stress flows are respectively 2.21 ml/min/g, 2.20 ml/min/g, 1.96 ml/min/g, and 2.47 ml/min/g, and the myocardial flow reserves are respectively 2.03, 2.37, 2.17, and 1.42. With reference to the blood flow condition diagram, the blood flow condition of the LAD area is represented by the colors of red and orange, the blood flow condition of the LCX area is represented by the color of orange, the blood flow condition of the RCA area is represented by the colors of orange and red, and the general blood flow condition of the LV area is represented by red (13.64%) and orange (86.36%).

EXAMPLE 2

Figure 10:
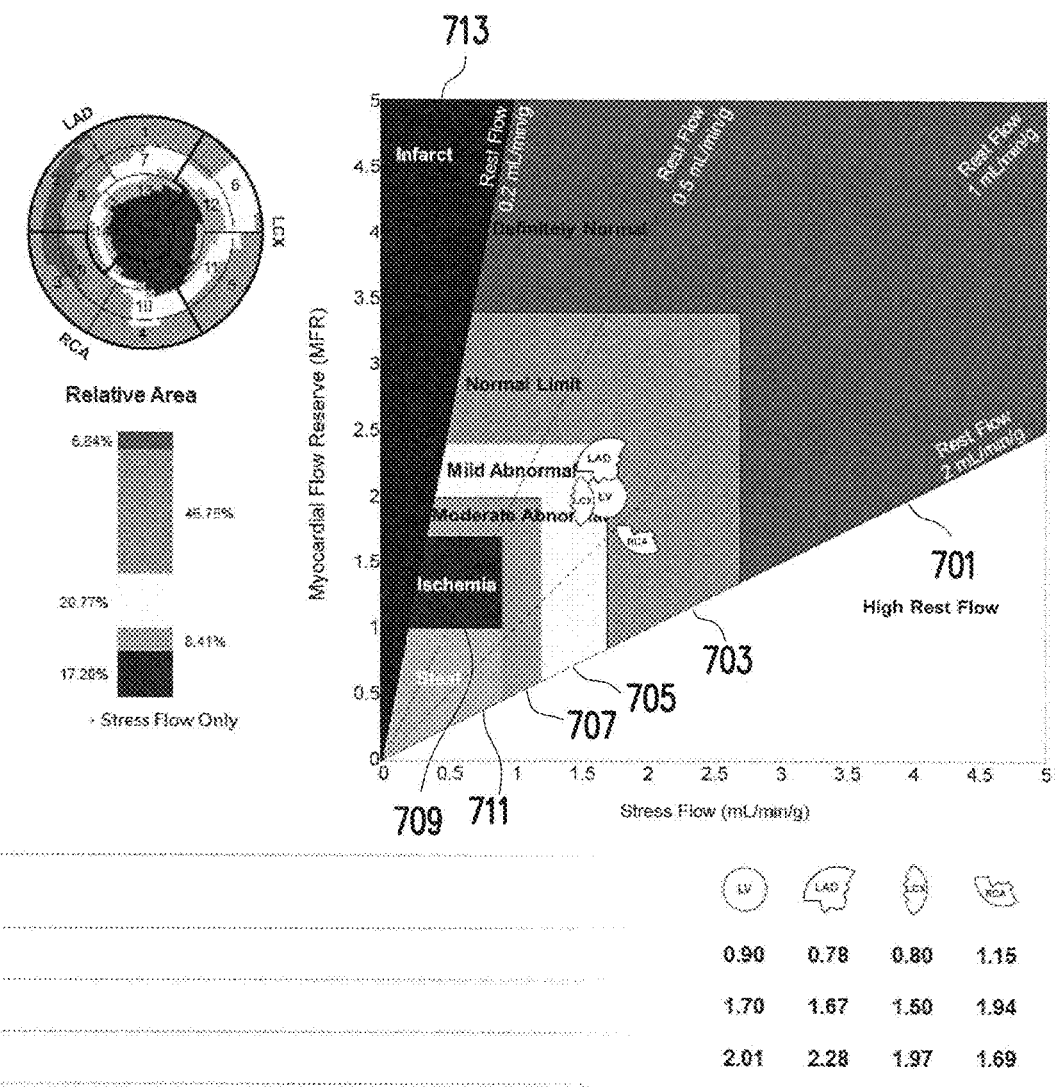
FIG. 10 is a schematic diagram illustrating Example 2 of the invention.

FIG. 10 is a schematic diagram illustrating Example 2 of the invention. FIG. 9 shows a 58-year-old male with a cardiovascular disease. Through the multi-pinhole dynamic SPECT quantitative image reconstruction, the absolute quantization of myocardial blood flow, and the blood flow condition evaluation according to the method in the embodiment of the invention, it is learned that in the left ventricular (LV) area, the left anterior descending (LAD) area, the left circumflex (LCX) area, and the right coronary artery (RCA) area, the rest flows are respectively 0.90 ml/min/g, 0.78 ml/min/g, 0.80 ml/min/g, and 1.15 ml/min/g, the stress flows are respectively 1.70 ml/min/g, 1.67 ml/min/g, 1.50 ml/min/g, and 1.94 ml/min/g, and the myocardial flow reserves are respectively 2.01, 2.28, 1.97, and 1.69. With reference to the blood flow condition diagram, the blood flow condition of the LAD area is represented by the colors of blue, green, yellow, orange, and red, the blood flow condition of the LCX area is represented by the colors of blue, green, yellow, orange, and red, the blood flow condition of the RCA area is represented by the colors of blue, green, yellow, and orange and the general blood flow condition of the LV area is represented by red (6.84%), orange (46.78%), yellow (20.77%), green (8.41%), and blue (17.20%). The examples show that the method according to the embodiment of the invention is capable of multi-pinhole dynamic SPECT quantitative image reconstruction, and is adapted for quantizing the myocardial blood flow and evaluating the flow rate of the myocardial blood flow.

Figure 11:
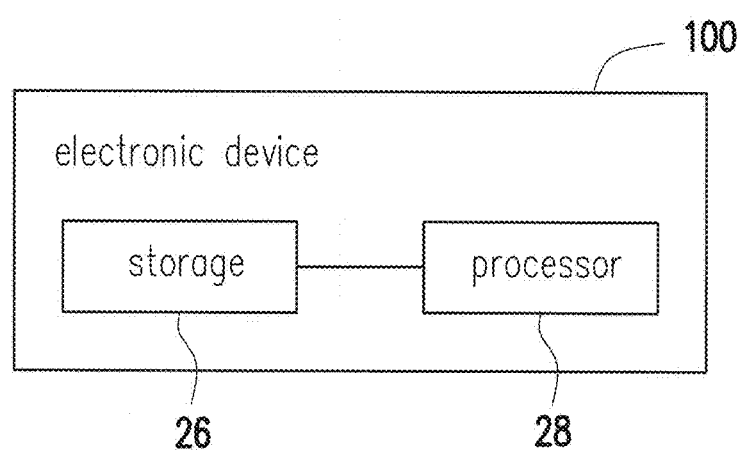
FIG. 11 is a block diagram illustrating an electronic device according to an embodiment of the invention.

FIG. 11 is a block diagram illustrating an electronic device according to an embodiment of the invention. It should be noted that an electronic device 100 shown in FIG. 11 may carry out the respective processes. The electronic device 100 may obtain the original projection image by any possible means and further carry out the radionuclide physical decay correction, the scatter correction, the geometry distortion correction, the data truncation compensation, the tissue attenuation correction, the image space resolution recovery, the noise removal, the pixel value conversion, the quantitative myocardial blood flow calculation, and the blood flow condition evaluation.

Referring to FIG. 11, the electronic device 100 of the embodiment includes a storage 26 and a processor 28. The storage 26 is coupled to the processor 28. The electronic device 100 is a cell phone, a tablet computer, or a notebook computer, for example. However, the invention is not limited thereto.

The storage 26 may be any kind of fixed or mobile random access memory (RAM), read-only memory (ROM), flash memory, other similar devices, or a combination thereof.

The processor 28 may be a central processing unit (CPU), or a programmable general purpose or specific purpose microprocessor, a digital signal processor (DSP), a programmable controller, an application specific integrated circuit (ASIC), other similar devices, or a combination thereof, for example.

In the exemplary embodiment, the storage 26 of the electronic device 100 stores a plurality of programming code segments. After being installed, the programming code segments are executed by the processor 28. For example, the storage 26 includes a plurality of modules. With the modules, the radionuclide physical decay correction, the scatter correction, the geometry distortion correction, the data truncation compensation, the tissue attenuation correction, the image space resolution recovery, the noise removal, the pixel value conversion, the quantitative myocardial blood flow calculation, and the blood flow condition evaluation are carried out. In addition, the respective modules include one or more programming code segments. However, the invention is not limited thereto. The respective processes of the electronic device 100 may also be carried out by hardware means.

Figure 12B:
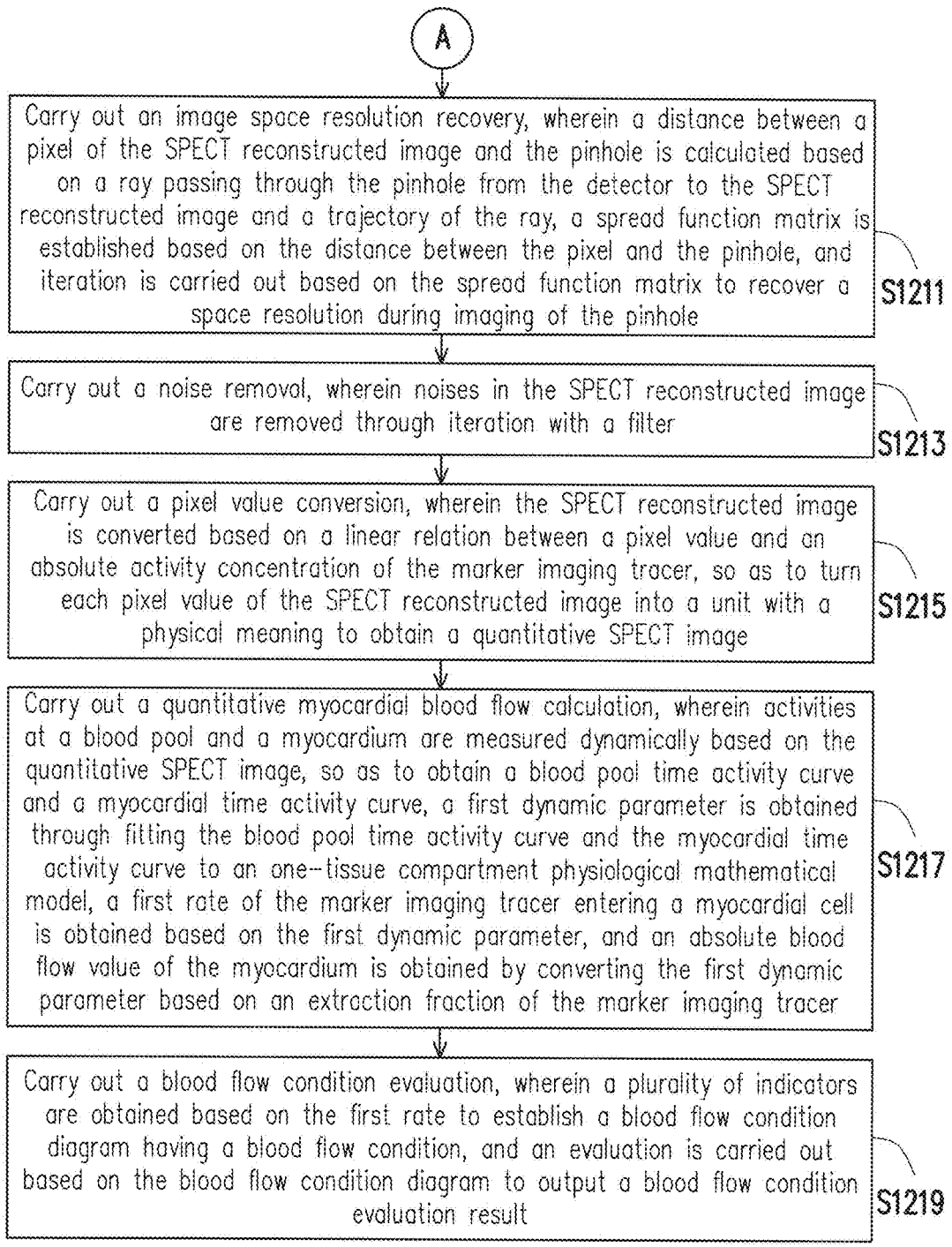

FIGS. 12A and 12B are flowcharts illustrating a quantitative method for a nuclear medicine heart image according to an embodiment of the invention.

Referring to FIGS. 12A and 12B, at Step S1201, the radionuclide physical decay correction is carried out to calculate the radionuclide decay correction coefficient at each dynamic time point in the dynamic SPECT collection based on the time point of starting the dynamic SPECT collection, the duration of the collection, and the half life of the marker imaging tracer. In addition, the radioactive count in the original projection image is corrected based on the radionuclide decay correction coefficient.

At Step S1203, the scatter correction is carried out to calculate the scatter component in the original projection image based on the scatter energy window. In addition, the scatter component is subtracted from the original projection image to obtain the original projection image after the scatter correction.

At Step S1205, the geometry distortion correction is carried out to translate the normal rays and perform the first coordinate conversion calculation through the forward projection and the back projection based on the geometric positions of the pinholes and detectors corresponding to the center of the SPECT reconstructed image, so as to obtain the correct positions of the oblique rays at the detectors and the SPECT reconstructed image. In addition, the geometry distortion in the SPECT reconstructed image resulting from the oblique rays is corrected.

At Step S1207, the data truncation compensation is carried out to calculate the truncated area in the field of view of the original projection image by expanding the field of the SPECT reconstructed image and carrying out another front projection. By combining the counts in the truncated area in the image projected from the SPECT reconstructed image with the original projection image to expand the field of view of the original projection image, and using the original projection image with the expanded field of view as the input for iteration to expand the field of view of the SPECT reconstructed image until convergence is reached, the artifact in the SPECT reconstructed image resulting from data truncation is corrected.

At Step S1209, the tissue attenuation correction is carried out to establish the tissue attenuation matrix by calculating the attenuation value of each ray emitted from the pinhole to the detector based on a tissue attenuation diagram. In addition, the underestimation of the marker imaging tracer extraction activity of the heart and the marker imaging tracer extraction activities of the parts other than the heart caused by tissue attenuation is corrected based on the tissue attenuation matrix, so as to correct the tissue attenuation in the SPECT reconstructed image.

At Step S1211, the image space resolution recovery is carried out to calculate the distance between the pixel of the SPECT reconstructed image and the pinhole based on each ray passing through the pinhole from the detector to the SPECT reconstructed image and the trajectory of the ray. Based on the distance between the pixel and the pinhole, the spread function matrix is established. In addition, based on the spread function matrix, the iteration is carried out to recover the space resolution during imaging of the pinhole.

At Step S1213, the noise removal is carried out to remove the noises in the SPECT reconstructed image through iteration with the filter.

At Step S1215, the pixel value conversion is carried out to convert the SPECT reconstructed image based on the linear relation between the pixel value and the absolute activity concentration of the marker imaging tracer. Accordingly, conversion of the SPECT reconstructed image turns each pixel value of the SPECT reconstructed image into a unit with a physical meaning, so as to obtain the quantitative SPECT image.

At Step S1217, the quantitative myocardial blood flow calculation is carried out to dynamically measure the activities at the blood pool and the myocardium based on the quantitative SPECT image. Accordingly, the blood pool time activity curve and the myocardial time activity curve are obtained. After fitting the blood pool time activity curve and the myocardial time activity curve to the one-tissue compartment physiological mathematical model, the first dynamic parameter is obtained. Based on the first dynamic parameter, the first rate of the marker imaging tracer entering the myocardial cell is obtained. In addition, by converting the first dynamic parameter based on the extraction fraction of the marker imaging tracer, the absolute blood flow value of the myocardium is obtained.

At Step S1219, the blood flow condition evaluation is carried out to obtain the indicators based on the first rate and thus establish the blood flow condition diagram having the blood flow condition. In addition, the evaluation is carried out based on the blood flow condition diagram to output the blood flow condition evaluation result.

In view of the foregoing, the quantitative method for the nuclear medicine heart image according to the embodiments of the invention is able to remove the respective physical interferences in the dynamic SPECT image, so as to obtain the quantitative image (unit of pixel value Bq/ml) equivalent to PET. Accordingly, the absolute quantization of myocardial blood flow is able to be calculated based on the methodology equivalent to that of PET. Therefore, quantization of myocardial blood flow becomes applicable in the myocardial blood flow condition evaluation.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A quantitative method for a nuclear medicine heart image, adapted for quantitative reconstruction of a multi-pinhole single-photon emission computed tomography (SPECT) or SPECT/CT image and an absolute quantization of myocardial blood flow, the method comprising:

carrying out an iterative image reconstruction, wherein an original projection image is obtained, and iteration is carried out to obtain an SPECT reconstructed image based on the original projection image, wherein the iterative image reconstruction comprises:

carrying out a geometry distortion correction, wherein a plurality of normal rays are translated and a first coordinate conversion calculation is performed through a forward projection and a back projection based on a geometric position of a pinhole and a detector corresponding to the center of the SPECT reconstructed image, so as to obtain correct positions of an oblique ray at the detector and the SPECT reconstructed image and correct a geometry distortion in the SPECT reconstructed image resulting from the oblique ray;

carrying out a data truncation compensation, wherein a truncated area in a field of view of the original projection image is calculated by expanding a field of view of the SPECT reconstructed image and performing another front projection, a count of a truncated area in an image projected from the SPECT reconstructed image is combined with the original projection image to expand a field of view of the original projection image, and iteration is performed with the original projection image having an expanded field of view as an input to expand the field of view of the SPECT reconstructed image until convergence is reached, so as to correct an artifact resulting from a data truncation in the SPECT reconstructed image;

carrying out a tissue attenuation correction, wherein a tissue attenuation matrix is established by calculating an attenuation value of each ray from the pinhole to the detector based on a tissue attenuation diagram, and underestimation of a marker imaging tracer extraction activity of a heart and marker imaging tracer extraction activities of parts other than the heart caused by tissue attenuation are corrected based on the tissue attenuation matrix, so as to correct the tissue attenuation in the SPECT reconstructed image;

carrying out an image space resolution recovery, wherein a distance between a pixel of the SPECT reconstructed image and the pinhole is calculated based on a ray passing through the pinhole from the detector to the SPECT reconstructed image and a trajectory of the ray, a spread function matrix is established based on the distance between the pixel and the pinhole, and iteration is carried out based on the spread function matrix to recover a space resolution during imaging of the pinhole; and carrying out a noise removal, wherein noises in the SPECT reconstructed image are removed through iteration with a filter;

carrying out a pixel value conversion, wherein the SPECT reconstructed image is converted based on a linear relation between a pixel value and an absolute activity concentration of the marker imaging tracer, so as to turn each pixel value of the SPECT reconstructed image into a unit with a physical meaning to obtain a quantitative SPECT image;

carrying out a quantitative myocardial blood flow calculation, wherein activities at a blood pool and a myocardium are measured dynamically based on the quantitative SPECT images, so as to obtain a blood pool time activity curve and a myocardial time activity curve, a first dynamic parameter is obtained through fitting the blood pool time activity curve and the myocardial time activity curve to an one-tissue compartment physiological mathematical model, a first rate of the marker imaging tracer entering a myocardial cell is obtained based on the first dynamic parameter, and an absolute blood flow value of the myocardium is obtained by converting the first dynamic parameter based on an extraction fraction of the marker imaging tracer; and carrying out a blood flow condition evaluation, wherein a plurality of indicators are obtained based on the first rate to establish a blood flow condition diagram having a blood flow condition, and an evaluation is carried out based on the blood flow condition diagram to output a blood flow condition evaluation result.

2. The quantitative method for the nuclear medicine heart image as claimed in claim 1, further comprising:

carrying out a radionuclide physical decay correction, wherein before the iterative image reconstruction, a radionuclide decay correction coefficient at each dynamic time point in a dynamic SPECT collection is calculated based on a time point of starting the dynamic SPECT collection, a duration of the collection, and a half-life of the marker imaging tracer and a radioactive count in the original projection image is corrected based on the radionuclide decay correction coefficient.

3. The quantitative method for the nuclear medicine heart image as claimed in claim 1, further comprising:

carrying out a scatter correction, wherein a scatter component in the original projection image is calculated based on a scatter energy window before the iterative image reconstruction, and the scatter component is subtracted from the original projection image to obtain the original projection image after the scatter correction.

4. The quantitative method for the nuclear medicine heart image as claimed in claim 1, further comprising:

carrying out an intra-scan patient movement correction, wherein after the iterative image reconstruction, based on the quantitative SPECT image at each dynamic time point and using the center of the heart as an origin, a second coordinate conversion, a ray tracing, and a geometric shape approximation are carried out to find boundaries of the blood pool and the myocardium, and a vector for correcting a movement of a patient is obtained based on a maximum correlation, and the quantitative SPECT image is corrected.

5. The quantitative method for the nuclear medicine heart image as claimed in claim 4, wherein the intra-scan patient movement correction further comprises:

converting the quantitative SPECT image from a Cartesian coordinate system to a spherical coordinate system through the second coordinate conversion, and converting the boundary of the myocardium from the spherical coordinate system back to the Cartesian coordinate system;

approximating the heart to a geometric shape by performing the geometric shape approximation; and using a position of the myocardium at the last dynamic time point as the reference, moving a position of the blood pool to calculate the maximum correlation between the position of the myocardium and the position of the blood pool.

6. The quantitative method for the nuclear medicine heart image as claimed in claim 1, wherein the geometry distortion correction further comprises:

respectively converting a normal ray passing through the pinhole and forward-facing the SPECT reconstructed image and a normal back ray forward-facing the detector into an oblique ray and an oblique back ray through the translation and the first coordinate conversion calculation based on the forward projection and the back projection, so as to obtain a correct position of the oblique ray at the detector and a correct position of the oblique back ray at the SPECT reconstructed image.

7. The quantitative method for the nuclear medicine heart image as claimed in claim 1, wherein the tissue attenuation correction further comprises:

obtaining an 140 keV attenuation coefficient of each pixel in the SPECT reconstructed image based on the tissue attenuation diagram, and calculating an attenuation value of the pixel of the SPECT reconstructed image corresponding to the detector with an exponential model and a linear integration based on a position of the SPECT reconstructed image corresponding to the pinhole and the detector to establish the tissue attenuation matrix.

8. The quantitative method for the nuclear medicine heart image as claimed in claim 1, wherein the image space resolution recovery further comprises:

considering the pinhole as a disc or having a geometrically symmetrical shape, calculating a distance between the pixel of the SPECT reconstructed image and the pinhole based on a common center of a plurality of rays passing through the pinhole from the detector to the SPECT reconstructed image and trajectories of the rays, and calculating a range and an area covered through spreading with distance based on a solid angle of the pinhole, so as to calculate the spreading coefficient matrix related to distances of the rays with respect to the disc.

9. The quantitative method for the nuclear medicine heart image as claimed in claim 1, wherein the noise removal further comprises:

carrying out iteration based on an analytic filter or a wavelet filter to remove the noises in the SPECT reconstructed image, and comparing the original projection image after filtering and a front projection image after filtering during the iteration to filter out noises, wherein the wavelet filter performs basis expansion on an image in a stationary mode, excludes a high-frequency expansion of coefficients with a fixed window in a histogram of expansion coefficients of different orders, and removes the noises in the SPECT reconstructed image by carrying out filtering the expansion coefficients with an analytic function.

10. The quantitative method for the nuclear medicine heart image as claimed in claim 1, wherein the blood flow condition evaluation comprises:

conducting an absolute quantization of myocardial blood flow based on the quantitative SPECT image, so as to obtain the indicators, and establishing the blood flow condition diagram with markings of different colors based on the indicators of rest flow, stress flow and myocardial flow reserve values measured from a group of people.

11. The quantitative method for the nuclear medicine heart image as claimed in claim 1, wherein the indicators in the blood flow condition evaluation comprise a stress flow, a rest flow, and a myocardial flow reserve.

12. The quantitative method for the nuclear medicine heart image as claimed in claim 1, wherein the quantitative myocardial blood flow calculation further comprises:

obtaining a second dynamic parameter and a third dynamic parameter through fitting the blood pool time activity curve and the myocardial time activity curve to the one-tissue compartment physiological mathematical model, obtaining a second rate of the marker imaging tracer exiting the myocardial cell based on the second dynamic parameter, and obtaining a third rate of the marker imaging tracer interacting with the myocardial cell based on the third dynamic parameter.

13. An electronic device for executing a quantitative method for a nuclear medicine heart image, comprising:

a storage storing a plurality of modules; and a processor, coupled to the storage and accessing and executing the modules stored in the storage to carry out the following:

an iterative image reconstruction, wherein an original projection image is obtained, and iteration is carried out to obtain an SPECT reconstructed image based on the original projection image, wherein the iterative image reconstruction comprises:

a geometry distortion correction, wherein a plurality of normal rays are translated and a first coordinate conversion calculation is performed through a forward projection and a back projection based on a geometric position of a pinhole and a detector corresponding to the center of the SPECT reconstructed image, so as to obtain correct positions of an oblique ray at the detector and the SPECT reconstructed image and correct a geometry distortion in the SPECT reconstructed image resulting from the oblique rays;

a data truncation compensation, wherein a truncated area in a field of view of the original projection image is calculated by expanding a field of view of the SPECT reconstructed image and performing a front projection, a count of a truncated area in an image projected from the SPECT reconstructed image is combined with the original projection image to expand a field of view of the original projection image, and iteration is performed with the original projection image having an expanded field of view as an input to expand the field of view of the SPECT reconstructed image until convergence is reached, so as to correct an artifact resulting from a data truncation in the SPECT reconstructed image;

a tissue attenuation correction, wherein a tissue attenuation matrix is established by calculating an attenuation value of each ray from the pinhole to the detector based on a tissue attenuation diagram, and underestimation of a marker imaging tracer extraction activity of a heart and marker imaging tracer extraction activities of parts other than the heart caused by tissue attenuation are corrected based on the tissue attenuation matrix, so as to correct the tissue attenuation in the SPECT reconstructed image;

an image space resolution recovery, wherein a distance between a pixel of the SPECT reconstructed image and the pinhole is calculated based on a ray passing through the pinhole from the detector to the SPECT reconstructed image and a trajectory of the ray, a spread function matrix is established based on the distance between the pixel and the pinhole, and iteration is carried out based on the spread function matrix to recover a space resolution during imaging of the pinhole; and a noise removal, wherein noises in the SPECT reconstructed image are removed through iteration with a filter;

a pixel value conversion, wherein the SPECT reconstructed image is converted based on a linear relation between a pixel value and an absolute activity concentration of the marker imaging tracer, so as to turn each pixel value of the SPECT reconstructed image into a unit with a physical meaning to obtain a quantitative SPECT image;

a quantitative myocardial blood flow calculation, wherein activities at a blood pool and a myocardium are measured dynamically based on the quantitative SPECT image, so as to obtain a blood pool time activity curve and a myocardial time activity curve, a first dynamic parameter is obtained through fitting the blood pool time activity curve and the myocardial time activity curve to an one-tissue compartment physiological mathematical model, a first rate of the marker imaging tracer entering a myocardial cell is obtained based on the first dynamic parameter, and an absolute blood flow value of the myocardium is obtained by converting the first dynamic parameter based on an extraction fraction of the marker imaging tracer; and a blood flow condition evaluation, wherein a plurality of indicators are obtained based on the first rate to establish a blood flow condition diagram having a blood flow condition, and an evaluation is carried out based on the blood flow condition diagram to output a blood flow condition evaluation result.

* * * * *